United States Patent [19]

Pieniak

[11] 4,333,782
[45] Jun. 8, 1982

[54] METHOD OF MAKING LAMINATED STRUCTURES HAVING GATHERED AND UNGATHERED MARGINAL PORTIONS

[75] Inventor: Heinz A. Pieniak, Chicago, Ill.

[73] Assignee: Johnson & Johnson Baby Products Company, New Brunswick, N.J.

[21] Appl. No.: 120,194

[22] Filed: Feb. 11, 1980

[51] Int. Cl.$^3$ .................... A61F 13/16; B32B 31/08
[52] U.S. Cl. .................... 156/164; 128/284; 128/287; 128/290 R; 156/229; 156/291; 156/301; 156/324
[58] Field of Search ............... 156/164, 163, 291, 324, 156/229, 292, 300, 301; 128/284, 287, 290 R; 2/237, 401

[56] References Cited

U.S. PATENT DOCUMENTS

| | | | |
|---|---|---|---|
| 3,788,365 | 1/1974 | Campbell et al. | 2/237 |
| 3,867,940 | 2/1975 | Mesek et al. | 128/284 |
| 4,069,822 | 1/1978 | Buell | 128/284 |
| 4,081,301 | 3/1978 | Buell | 156/164 |

Primary Examiner—Jerome W. Massie
Attorney, Agent, or Firm—Martha A. Michaels

[57] ABSTRACT

A laminated structure having a marginal area with gathered and ungathered portions which provide an improved fit about a portion of the human body, said laminated structure comprising an elastic member disposed between first and second substrates of flexible gatherable material, said elastic member comprising a plurality of longitudinally extending elastic elements with the elements transversely connected over a portion of their length to define apertures and an end portion of the member comprising only longitudinally extending elements and the first and second substrates of said laminated structure being secured together through at least some of said apertures.

3 Claims, 12 Drawing Figures

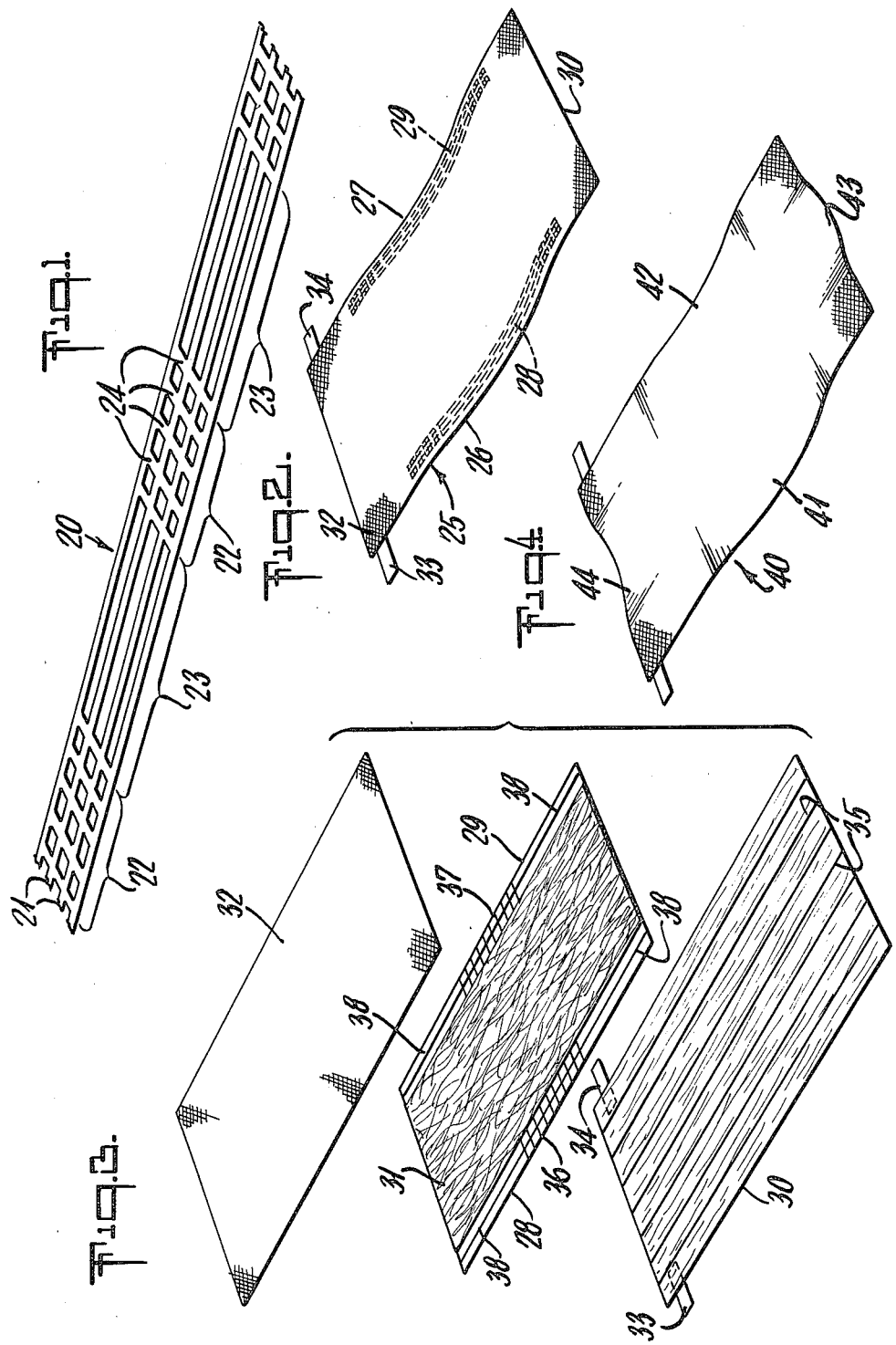

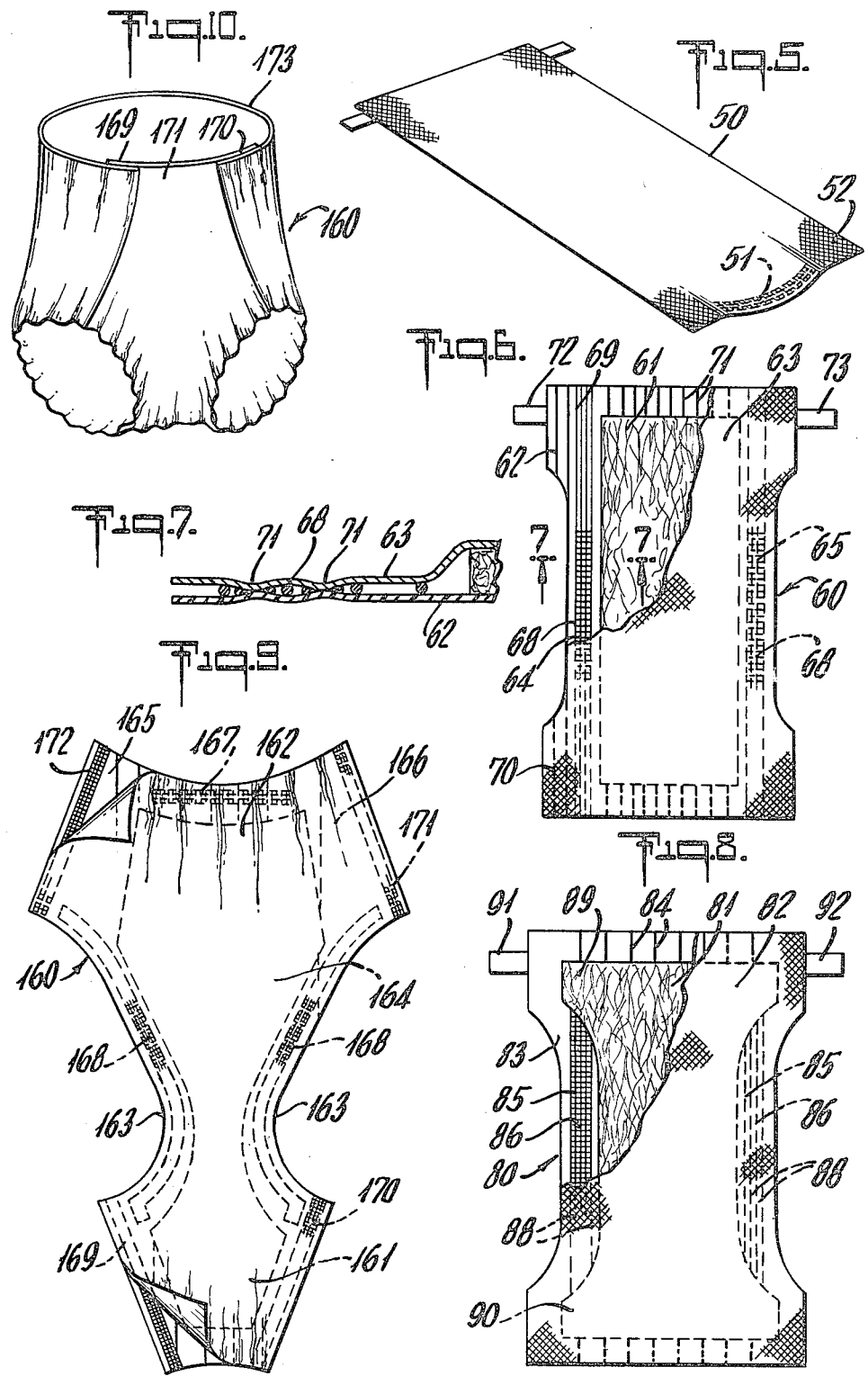

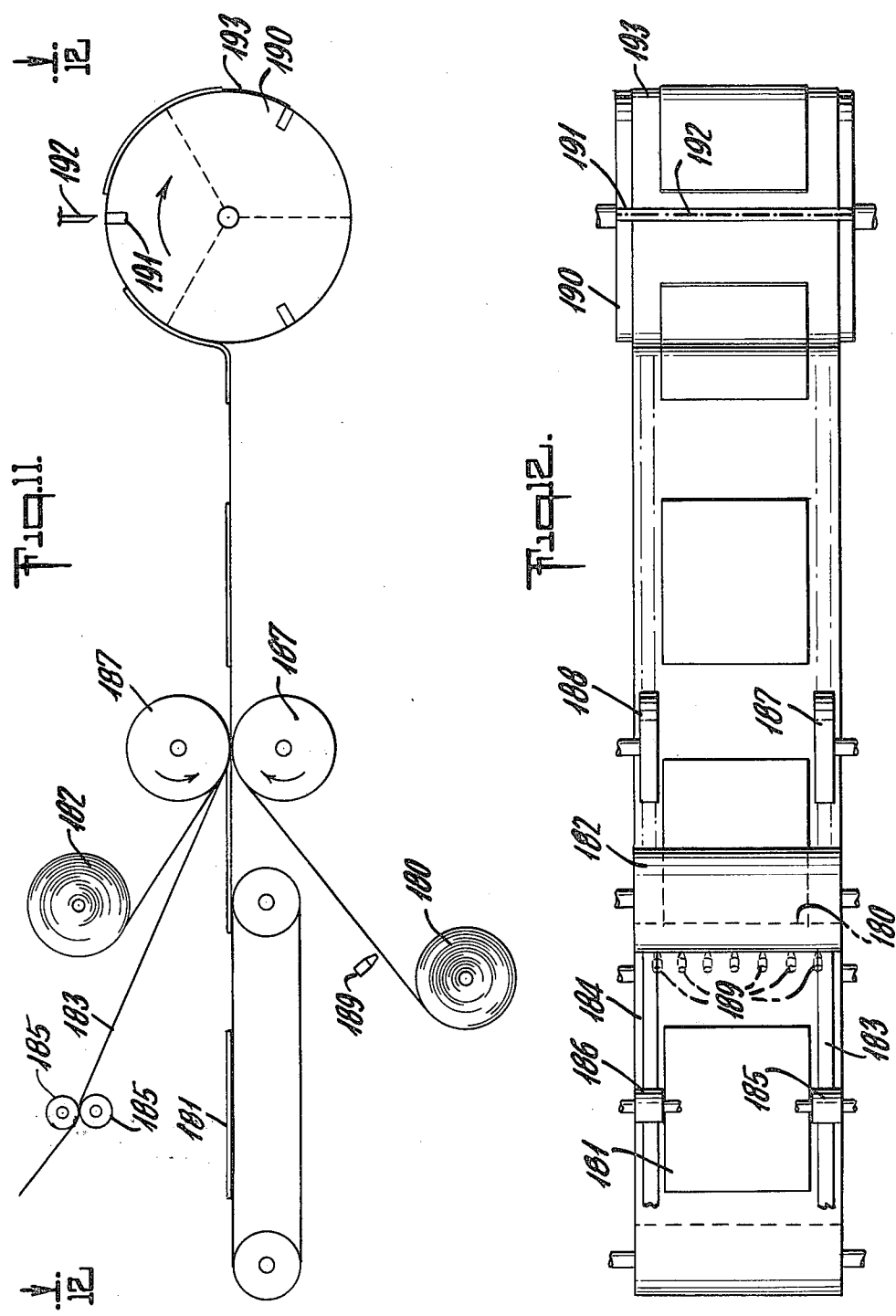

METHOD OF MAKING LAMINATED STRUCTURES HAVING GATHERED AND UNGATHERED MARGINAL PORTIONS

BACKGROUND OF THE INVENTION

Recent years have seen an increased demand for inexpensive apparel and the development of new and inexpensive components of construction and methods of construction of articles of apparel. In certain instances, there is a demand for apparel that is very inexpensive and, indeed, disposable. New elastomeric materials and methods of incorporating them into portions of a garment have been developed to meet the desire to fit these types of garments to a human form. For example, U.S. Pat. No. 3,639,917 discloses the use of a strip of a heat recoverable elastomeric material to gather the cuff of a disposable hospital gown.

Disposable diapers have been marketed which include an elastic or stretch member in the longitudinal side edges of the disposable diaper to provide elasticity about the leg of the infant when the diaper is applied. Examples of such stretchable fitted diapers which have elastic members disposed in the longitudinal side edges of the diaper are shown in U.S. Pat. Nos. 3,860,003 and 4,050,462. By being able to elastically contract the longitudinal sides of the diaper which are the leg and thigh encircling portion of the diaper once placed on an infant, you can compress the diaper about the leg of the infant. By virtue of this compressing, you reduce leakage at the leg of the infant and the tighter you make the fit, the more you tend to reduce leakage. However, if the fit is too tight, you will cause irritation on this tender portion of the thigh, especially when the diaper is wet. There are also a number of patents which disclose means for making the waist encircling portion of a disposable diaper elastic for tighter fit of the diaper about the waist of the wearer, for example, as shown and described in U.S. Pat. Nos. 3,995,637 and 3,995,640.

Disposable diapers usually comprise a facing and a backing layer which is substantially co-extensive and a somewhat smaller absorbent core or panel interposed between the facing and backing layer. The facing and backing layers are adhered together about their perimeter by hot melt adhesive or other adhesive material as is well known. In producing stretch or elastic diapers, an elastic member in its stretched or partially stretched state, is interposed between the facing and backing sheets along one or more edges of the diaper. The elastic member is adhered either to the facing and/or the backing sheets by adhesive or similar means and allowed to relax to produce elastic sections at the edges of the diaper. An example of a method for inserting elastic members in disposable diapers is disclosed in U.S. Pat. No. 4,081,301.

The incorporation of these elastic members into disposable diapers has increased both the cost of materials used in the diaper and the cost of construction of disposable diapers. With solid elastic members, it is necessary to adhere the side edges of the facing and backing sheets together, either directly or by their mutual attachment to the elastic member.

When adhesively securing such an elastic member into a disposable diaper, the adhesive chosen must be elastomeric or must be applied in a discontinuous pattern or the glue may make the diaper too stiff to gather.

In commonly assigned co-pending patent application, Ser. No. 60,704, filed July 25, 1979, now abandoned there is disclosed apertured elastic members which have substantial advantages over other types of elastic members in that they are simpler and more economical to insert and function very well by providing a good fit with a minimum of irritation. The present invention is an improvement on such apertured elastic members.

SUMMARY OF THE INVENTION

What I have discovered is an improved laminated structure having a marginal area with a gathered portion and an ungathered portion which provide improved fit about a portion of a human body and a method of making the same. The laminated structure comprises first and second substrates of flexible, gatherable material and an elastic member disposed between the substrates in the marginal area thereof. The elastic member comprises a plurality of longitudinally extending elastic elements. The longitudinal elements are transversely connected over a portion of their length and define apertures therebetween. The first and second substrates are secured together through at least some of the apertures.

An end portion of the elastic member has only longitudinally extending elements; i.e., these elements are not transversely connected or interconnected. The transversely connected elements provide a gathered marginal portion and the non-interconnected elements provide an ungathered marginal portion.

The laminated structure of the present invention may be used in any fitted garment but perhaps is most suited for use in inexpensive and disposable apparel. The laminated structure can be incorporated into the sleeve cuff, the leg encircling portion, about the neck, and the waist of an article of apparel. In particular, the laminated structure may be incorporated into both the waist and thigh encircling portions of a disposable diaper or other disposable undergarments. The improved laminated structure of the present invention reduces the pressure applied to the skin of the wearer and, in a disposable diaper or a disposable undergarment reduces the possibility of irritation and rash when wet.

In accordance with the present invention, the new and improved elastic member can be readily inserted in a stretched condition between the first and second substrates and these substrates easily adhered together to hold the elastic member in place, at high speeds, with good reliability and at reduced costs. Surprisingly, when the new and improved elastic member is severed in the area of the member where the longitudinally extending elastic elements are not transversely connected or interconnected, these unconnected portions of the elements will relax and contract to their original unstretched state and will not gather the substrates; whereas, the interconnected or apertured portion of the elastic member will act to gather the substrates.

The elastic member has a width of from about ¼ inch to about 2 inches and the member may have a thickness of from 1 to 50 mils and preferably from about 5 to 20 mils. The elastic member may be made of any of the standard film materials which are stretchable and are recoverable and have a modulus of elasticity at 100 percent elongation of from about 20 to 2000 lbs./sq. inch. In a disposable diaper in accordance with the present invention, the elastic member may be disposed between the backing and facing sheet of the diaper in the longitudinal side margins of the diaper.

In a preferred embodiment of a disposable diaper of the present invention, the central portion of the elastic member comprises interconnected longitudinally extending elastic elements which define apertures and this central portion acts to gather the side margin of the diaper. The two end portions of the elastic member comprise non-interconnected longitudinally extending elements in a relaxed and unstretched state and which do not act to gather the side margins of the diaper.

In one method of the manufacture of a disposable diaper incorporating the laminated structure of the present invention, the facing and backing sheets of the diaper are adhesively secured together as in the past; i.e., adhesive is placed on the backing and the absorbent core is secured to the central portion of the backing sheet and the facing sheet is adhered at the edges. The elastic member is disposed in one or more of the edges of the backing and the adhesive disposed on the backing is allowed to adhere to the facing sheet through the open areas of the elastic member.

In the production of disposable diapers in accordance with one embodiment of the present invention, a continuous web has lines of adhesive placed on its surface. Absorbent batts are placed in spaced relationship along with web. Elastic members in a stretched condition are disposed along each longitudinal edge of the continuous web. The elastic members have alternating interconnected portions and non-interconnected portions as previously described. The elastic members are positioned so that an interconnected portion is placed adjacent approximately the center third or so area of an absorbent batt with a non-interconnected portion extending to approximately the center third or so area of the adjacent batt. A second continuous web is placed on top of the batt and is urged against all of the marginal areas surrounding the batt to be secured to the bottom web by the exposed adhesive lines. The two webs are secured together through the open areas in both the interconnected and non-interconnected portions of the elastic members. Individual diapers are produced by severing this laminate between absorbent batts. In so doing, the elastic member is severed in a non-interconnected area and when severed the elastic member contracts. The interconnected portion of the elastic member gathers the longitudinal side margin of the diaper and the non-interconnected portions of the elastic member relax and contract to an unstretched state without gathering the side margin of the diaper.

It should be pointed out that by using the elastic members in accordance with the present invention, the insertion of the member into the product and the adherence thereto is greatly simplified and, hence, has considerable economic benefit in the manufacturing process. The apertured portion insures a uniform, intermittent lamination between the elastic and non elastic layers and combined with the non-interconnected portions reduces the criticality of adhesive application. Also, the apertures combined with adhesion of the layers through these apertures provides that the final lamination acts or performs in its stretch, recovery and similar elastic properties substantially the same as the original elastic member, thus allowing for greater certainty in predicting the quality and functionality of the final product.

BRIEF DESCRIPTION OF THE DRAWINGS

In the drawings:

FIG. 1 is an enlarged perspective view illustrating an elastic member which may be used in accordance with the present invention;

FIG. 2 is a perspective view illustrating a disposable diaper in accordance with the present invention, with the diaper laid out flat;

FIG. 3 is an exploded perspective view showing relative positioning of the diaper elements depicted in FIG. 2;

FIG. 4 is a perspective view of another embodiment of the disposable diaper embodying the present invention;

FIG. 5 is a perspective view showing still another embodiment of the disposable diaper embodying the present invention;

FIG. 6 is a plan view of one embodiment of the disposable diaper of this invention with a portion broken away to show interior detail;

FIG. 7 is an enlarged cross-sectional view taken along line 7—7 of FIG. 6;

FIG. 8 is a plan view of another embodiment of the disposable diaper of this invention with a portion broken away to show interior detail;

FIG. 9 is a plan view of a disposable undergarment laid out flat, in accordance with the present invention with portions folded back to show interior detail;

FIG. 10 is a perspective view of the disposable undergarment of FIG. 9 viewed in the configuration it assumes when disposed about a wearer;

FIG. 11 is a schematic representation in side elevation of one embodiment of a method of assembling the components of a disposable diaper according to the present invention; and FIG. 12 is a simplified plan view of the schematic representation shown in FIG. 11 taken along new line 12—12 in FIG. 11.

DESCRIPTION OF THE PREFERRED EMBODIMENTS

For a laminated structure of the present invention, the elastic member is a readily stretchable, preferably thermoplastic member that possesses a certain minimum elastic recovery.

The term "elastic" as used herein, refers to sheets, films, ribbons, filaments, and the like which have a recovery of at least 90 percent, when enlongated to within 10 percent of their field Point and measured in accordance with the following formula:

$$\text{Percent retraction} = \frac{L_e - L_t}{L_e - L_o} \times 100$$

where;
- $L_o$ = original length of sample
- $L_e$ = fully extended length
- $L_t$ = length of sample measured three seconds after release from extended length The thickness of the elastic member may be from about 1 to 50 mils and is preferably from about 5 to 20 mils. They have a width of from ¼ inch to 2 inches and preferably in diaper applications widths of from ½ inch to 1 inch have been found satisfactory. For ease of stretchability, the modulus of elasticity of the elastic member at 100 percent elongation should not exceed about 2000 lbs./sq. inch. The modulus of elasticity is preferably substantially less than 2000 lbs./sq. inch, and most preferably is about 75 to about 400 lbs./sq. inch.

As shown in FIG. 1, the elastic member 20 useful in accordance with the present invention comprises a plurality of longitudinally extending elastic elements 21. These elements are transversely connected in intermittent areas 22 of the member which areas alternate with areas 23 wherein the longitudinally extending elastic elements are not transversely connected. The transversely connecting members 24 may or may not be elastic. However, as will be hereinafter described, the elastic members are preferably made from a single component and, hence, the properties of the member are substantially uniform throughout the member. The opening in the transversely connected areas 22 may have any shape such as square, oval, round, rectangular, triangular, or the like. Either square or rectangular shaped openings are preferred with the longitudinal and transverse elements perpendicular to each other. This configuration virtually eliminates any "necking down", reduction in the transverse dimension when the member is stretched longitudinally, and hence facilitates insertion of the member with the product and the adhesion of the layers of the laminate through the openings in the elastic member. The openings in the non-transversely connected areas 23 are usually very long, narrow areas. Depending on the modulus of elasticity of the material used and the thickness and width of the member, the number of openings in the transversely connected areas may vary from two to 100 openings per linear inch in both the longitudinal and transverse direction of the member. In addition, the elastic elements in the longitudinal direction may be of different widths, sizes or even shapes as compared to the elements in the transverse direction, and the spacing between the elastic elements may vary from the transverse to the longitudinal direction.

Referring to FIG. 2, a disposable diaper 25 embodying the present invention has longitudinal side margins 26 and 27. The central portion of each side margin is gathered to provide improved fit about the baby's thighs. The elastic member 28 and 29 in each of the longitudinal side margins is an elastic member according to the present invention. Individual components of the disposable diaper of FIG. 2 are illustrated in FIG. 3. The diaper additionally includes a first layer or backing layer 30 made of a moisture-impermeable material, a rectangular absorbent batt 31 superimposed over backing layer 30 and secured thereto by a series of glue lines 35 deposited on the backing layer, and a second layer or facing layer 32 made of a moisture-permeable web and positioned in superimposed relationship to the absorbent batt. The absorbent batt is of smaller area than the backing and when substantially centered to the backing, is spaced from the longitudinal sides as well as the transverse ends of the diaper. The absorbent batt is flanked on its longitudinal sides by elastic members 28 and 29 located generally parallel the longitudinal edges of the batt and which, in an extended state, are secured between the backing and the facing by means of the adhesive lines 35. A moisture-pervious facing 31 is superimposed over the absorbent batt and secured to the backing by means of the end and side portions of the glue lines 35. The facing is also secured to the backing between the openings in the elastic member. For securing the diaper about a baby, the diaper is provided with pressure-sensitive tape tab members 33 and 34.

In the manufacture of the diaper, only the central portions 36 and 37 of the elastic members 28 and 29 act to gather the longitudinal side margins of the diaper. The end portions 38 which comprise the non-transversely connected portions of the elastic members, merely "snap back" to a relaxed, unstretched state and do not act to gather the diaper. The use of the elastic member of the present invention provides a reduction in cost of materials over a solid elastic member of the same length and width used to apply a gathering force to the longitudinal side margins.

The elastic member of the present invention may be produced by a variety of methods such as passing an appropriate stretchable and recoverable film between the nip of a pattern forming roll and a back-up roll in a procedure analogous to that shown in U.S. Pat. Nos. 3,881,381 and 3,632,269. When using such a procedure, the pattern of the forming roll should be altered to provide for the alternating areas of transversely connected longitudinally extending elements and non-transversely connected longitudinally extending elements. However, if a uniform pattern is used as disclosed in the above-mentioned patents, it is a simple matter to merely sever the transversely connecting elements between longitudinal elements to render the longitudinal elements unconnected or even remove the transverse elements in certain areas to render those areas not transversely connected.

FIG. 4 shows another disposable diaper 40 similar to that shown in FIG. 2 with the exception that all four edge portions; that is, the two longitudinal side margins 41 and 42 and the front 43 and rear 44 end portions are elastic members in accordance with the present invention inserted between the facing and the backing with the central portions thereof elastic.

FIG. 5 shows a disposable diaper 50 similar to the diaper depicted in FIG. 2 with the exception that the reticulated elastic member 51 is only in the central front waist portion 52 of the diaper to provide improved fit about the baby's waist.

In the embodiment shown in FIG. 6, a disposable diaper 60 is provided with a substantially rectangular panel 61 sandwiched between a backing 62 and facing 63 and together with the backing and facing define side margins 64 and 65. Curvilinear cut-outs are provided in the respective central side portions of the facing and backing for further fit enhancement. Pre-stretched elastic members 68 are positioned in the longitudinal side margins and are secured between the backing and facing along the longitudinal sides of the absorbent panel. The elastic members have been relaxed and retracted from their original end position at 69 and 70. Glue lines 71 secure the facing and absorbent panel to the backing and adhesive tape tabs 72 and 73 provide diaper securement means.

Referring to FIG. 7, which is a cross-sectional view taken along 7—7 of FIG. 6, there is shown the impervious backing member 62 with the elastic member 68 secured between the backing member and the facing member 63 by the glue lines.

In the embodiment shown in FIG. 8, the disposable diaper 80 is provided with an absorbent batt 81 and also having curvilinear side cut-outs and sandwiched between facing 82 and backing 83 having similar cut-outs. Glue lines 84 serve to secure the batt and facing to the backing. Elastic members 85 are situated in the general rectilinear diaper side margins. The elastic members are secured between the facing and backing at the central portion 86 by adhesive lines 88 which may be applied at the same time as, and may lie along the same line as certain of the glue lines 84.

Protruding portions 89 and 90 of the absorbent batt overlap into the four corners of the diaper.

The elastic members suitable for use in the diapers contemplated may be made from films extruded, calendered, or otherwise formed to the desired thickness and pattern of openings utilizing low stretch modulus materials made from any rubbery elastic material. Specifically unvulcanized thermoplastic compositions which are made of an elastomeric component and an optional compatible modifier which is a thermoplastic polymer of a relatively low molecular weight but solid at ambient temperatures have been found to make suitable elastic members for use in accordance with the present invention.

Illustrative of the elastomeric components suitable for present purposes are block copolymers which comprise terminal thermoplastic polymer blocks and at least some non-terminal or intermediate elastomeric polymer blocks. Block copolymers of this general type may be prepared using a step-wise polymerization initiator; e.g., an organolithium compound. Such block polymerization techniques are well known in the art.

The elastic component can be linear or radial $A^1$-B-$A^2$ block copolymers or mixtures thereof with simple $A^1$-B block copolymers wherein $A^1$ and $A^2$ can be alike or different and represent a thermoplastic polymer block, such as poly(vinyl arene) block, and B represents an elastomeric polymer block such as a conjugated diene or a lower (i.e., $C_1$-$C_4$) alkene. The modifier component is a low molecular weight thermoplastic polymer having an average molecular weight of about 500 to 7,500 and is present in the composition in an amount of about zero to about 200 parts by weight per 100 parts by weight of the elastomeric component.

A preferred thermoplastic film composition for the elastic members comprises an elastomeric component which contains, as a major constituent thereof, an unvulcanized linear block copolymer of the general configuration, $$A^1-B-A^2$$

wherein $A^1$, $A^2$ and B have the same meaning as hereinabove. In these block copolymers, the A-blocks are derived from styrene or styrene homologues, and the B-blocks are derived from conjugated dienes or lower alkenes. The thermoplastic polymer modifier is compatible with the elastomeric component and associates principally with the thermoplastic terminal blocks of the aforesaid unvulcanized block copolymer. The thermoplastic polymer modifier preferably has an average molecular weight of about 1000 to about 3000, and is present in the film composition in an amount of about 80 to 200 parts by weight per 100 parts by weight of the elastomeric component.

The preferred $A^1$-B-$A^2$ block copolymers have A-blocks derived; i.e., polymerized or copolymerized, from styrene or styrene homologues; and B-blocks derived from conjugated dienes, such as isoprene or butadiene, or from lower alkenes such as ethylene and butylene. Small proportions of other monomers also may enter into the block copolymers themselves. The individual A-blocks can have an average molecular weight of at least about 6000, preferably in the range of about 8000-30,000, and the A-blocks constitute about 5-50 percent, preferably about 10-30 percent, by weight of the block copolymer. The average molecular weight of the B-blocks for linear $A^1$-B-$A^2$ block copolymers preferably is in the range of about 45,000-180,000 and that of the linear copolymer, itself, preferably is in the range of about 75,000-200,000. The average molecular weight of the radial $A^1$-B-$A^2$ block copolymers preferably is in the range of about 125,000-400,000. The term "linear block copolymer" (or copolymers) includes branched $A^1$-B-$A^2$ copolymers as well as unbranched $A^1$-B-$A^2$ copolymers. The radial $A^1$-B-$A^2$ copolymers useful for manufacture of elastic members for diapers of this invention are of the type described in U.S. Pat. No. 3,281,383 to Zelinski, et al. and conform to the following general formula: $(A-B-_n-X)$, wherein A is a thermoplastic block polymerized from styrene or styrene homologues, B is an elastomeric block derived from conjugated dienes or lower alkenes, as indicated above, X is an organic or inorganic connecting molecule, with a functionality of about two to four as described in U.S. Pat. No. 3,281,383, or possibly with a higher functionality as described in the Article entitled "New Rubber Is Backed By Stars" appearing on Page 35 of the June 11, 1975, issue of Chemical Week. As used hereinabove, "n" has a value corresponding to the functionality of X.

The preferred elastic member is highly thermoplastic and, though elastomeric, is unlike rubber in that it exhibits a relatively sharp melting point and is capable of being heat shaped. Also, the elastic member can form permanent heat seals to substrates such as non-woven fabrics or the like, at relatively low heat sealing temperatures, generally not above about 350° F. The member is very flexible, extensive and soft, and normally exhibits a Gurley stiffness of about one or less at a film thickness of one mil.

Elastic members especially suitable for use in disposable diapers may be made from combinations of thermoplastic rubber and amorphous polypropylene. The thermoplastic rubbers used in such combinations are block copolymers having blocks of polybutadiene or polyisoprene, and blocks of polystyrene. A review article discussing these materials is "Structure And Properties Of Block Polymers And Multi-phase Polymer Systems: An Overview of Present Status And Future Potential", by S. L. Aggarwal, *Polymer*, Vol. 17, November 1976, Pages 938-956. Two representative types of thermoplastic rubbers useful in these combinations are the linear block copolymers (A-B-A) having a mid-block of polybutadiene or polyisoprene and end-blocks of polystyrene, and the "star" or "radial" block copolymers having from 4 to 20 "arms" connected to a common center. Each arm is an A-B block copolymer, the inner portion being polybutadiene or polyisoprene, with the outer portion being polystyrene.

The material added or combined with the thermoplastic rubber, primarily to improve process ability, while still retaining the characteristic rubbery properties of the rubber, is amorphous polypropylene. Amorphous polypropylene is a known material. It is essentially atactic polypropylene having an isotactic content of not more than about 20 weight percent, and preferably not more than about 10 weight percent.

The amorphous polypropylene is employed in an amount sufficient to improve the processability of the thermoplastic rubber when extruding thin films or sheets. The exact minimum amount of amorphous polypropylene which must be employed varies somewhat for case to case, but it is usually of the order of about 10 weight percent, based on weight or rubber plus amorphous polypropylene, although the proportion may be as low as about 5 weight percent (on the same basis) in some cases. The upper limit of polypropylene will also vary from case to case, depending on the nature of the ingredients and the use intended for the product. At proportions above about 35 weight percent (on the same basis), a significant reduction in the characteristic rubbery elastomeric properties of the product begins to occur. This may be acceptable for some uses, and not for others. Thus, the upper limit of amorphous polypropylene would be that point at which the product still retains significant rubbery elastomeric characteristics.

Other conventional materials, employed in the usual amounts, can be employed in the mixture for their known purposes. Such materials include pigments, antiblocking agents, stabilizers, anti-oxidants, ultraviolet stabilizers, bonding aid, and the like.

In some embodiments of the disposable diaper of the present invention, the elastic member is a member which may be made elastic by imparting heat or other forms of energy to the member to shrink the member and provide it with elastic characteristics.

The heat shrinkable films which may be used as elastic members in the disposable diapers of the present invention may be the polyolefin films which have been oriented to a degree and which will then become elastic when heat shrunk. Usually, a preferred technique for orienting the polyethylene film to provide the heat shrunk elastic properties is by irradiation such as suggested in British Pat. No. 866,820. Also, useful as the heat shrunk elastic members are the copolymers of ethylene and vinyl acetate, ethylene and ethyl acrylate, and the like. The forming of such copolymers is well known and specific methods of forming such materials are disclosed in U.S. Pat. Nos. 2,200,429 and 2,953,551. After the copolymer is formed and made into a film, it is given the proper orientation as described in the previously mentioned British Pat. No. 866,820.

The elastic member useful in accordance with the present invention may also be made from other materials; such as, natural rubber, the synthetic rubbers, and the like.

Broadly, the elastic members may be made from materials having elongations of from 20 to 1000 percent and preferably from about 50 to 500 percent with recoveries in the range of 20 to 100 percent and preferably from 70 to 100 percent. The material should have a force to stretch it 100 percent of from 30 to 2000 grams.

The important factor to remember is that when the material is placed in the end product, the material be elastic, as previously defined, so it functions as such an elastic in the final product. For example, in the diaper leg band area, the member should have 90 percent or better recovery in very short periods of time and preferably almost instantaneously, the member should also require a relatively low amount of force to stretch the leg band area back to its original or non-gathered length. Such force should be less than 200 grams and may be as low as 20 grams.

FIG. 9 illustrates a disposable undergarment 160 suitable for use in toilet training infants, or by incontinent children or adults. The undergarment has a front portion 161, a rear portion 162, and a crotch portion 163 comprised of an intermediate liquid absorbent panel 164 disposed between outer layer 165 and a moisture-permeable inner layer 166. The waistband of the undergarment may be gathered by an elastic member 167 located between the ends of the inner and outer layers at the rear portion and optionally between the ends of the inner and outer layers at the front portion. The undergarment may also be provided with elastic members 168 disposed between the inner and outer layers at the side margins of the crotch region.

FIG. 10 illustrates the disposable undergarment 160 of FIG. 9 about a wearer in use; both side margins 169 and 170 of the front portion being joined to respective side margins 171 and 172 of the rear portion to define a waist portion 173 and self-fitting leg apertures 174.

Several different types of facing materials may be used for the disposable undergarment, for example, the facing may be a non-woven web made of a mixture of fibers consisting predominantly of inexpensive, short, cellulosic fibers such as short wood pulp fibers or cotton linters in amounts of 75 percent to 98 percent, the balance being textile length fibers such as rayon as described in U.S. Pat. No. 3,663,348 to Liloia, et al.

Non-woven facing materials suitable for use in disposable undergarments of this invention can have fabric weights in the range of from about 0.5 to 5 ounces per square yard and densities of less than 0.15 g/cc., generally in the range of 0.05 to about 0.1 g/cc. The dry strength of the facing sheet for a fabric having a weight of about 1.5 ounces per square yard is at least 0.15 lbs. per inch of width in the machine direction and at least 0.1 lb. per inch of width in the cross direction. Such fabrics have good elongation, loft, softness, and drape characteristics. Facings may also be made of an apertured non-woven fabric which is formed, for example, in accordance with the teachings of commonly assigned U.S. Pat. Nos. 2,862,251; 3,081,514; and 3,081,515. Furthermore, facings may also be made from other types of fabric such as those disclosed and described in U.S. Pat. No. 3,485,706 to Evans. Such facings can be made of naturally occurring fibers, synthetic fibers or blends thereof. Typical facing sheets made of polyester type fibers may have a weight of about 0.75 ounces per square yard.

The facing may be the same size as, and coterminous with, the backing; or alternatively, the facing may be wider than the backing and have its side edges inwardly folded so that the facing is coterminous with the backing, as is shown in FIG. 3 of U.S. Pat. No. 3,612,055. In the latter case, the elastic members may be secured above the inwardly folded side edges of the facing. In addition, facings may be made from non-apertured materials such as non-woven isotropic webs or apertured polyolefin or polyester films having the desired moisture permeability. In all of the aforementioned facings, the materials should be relatively hydrophobic so as to retard wicking within the facing.

The moisture absorbent batt or panel of a desired shape, but smaller than the facing and backing, can be formed in accordance with the teachings of U.S. Pat. No. 3,612,055 to Mesek, et al.

A suitable backing material for the disposable undergarments embodying the present invention can be an opaque polyolefin; for example, polyethylene about 0.001 inch thick. Another suitable material for this purpose is polyethylene terephthalate having a thickness of about 0.005 inch.

In use, the disposable diaper is applied to the baby by laying out the diaper on a single flat surface and placing the baby thereon. The waist underlying end of the diaper is that end having the fastener means and the other end of the diaper extends downwardly between the baby's legs. Next, the downwardly extending edge of the diaper is brought up between the baby's legs to a position covering the perineum and contiguous with the front portion of the baby's waist. The diaper thereafter is secured to the baby by placing the corners of the waist portion of the abdomen covering end as far around the baby's waist as they will go and by bringing the corners of the underlying end of the diaper into an overlapping relationship with the aforementioned corners so that the diaper snugly encircles the baby's waist and provides a custom fit. The adhesive tape fasteners are then prepared for use and the diaper is brought in a desired position by simply urging the pressure-sensitive adhesive surface of the tape tab in contact with the adjacent outer surfaces of the opposite corner of the diaper.

In some instances, it may be desirable to have a second fastener available that can be applied just above the thigh of the infant and below the standard fastener to improve and secure the fit of the stretch diaper.

A technique that may be used in the manufacture of the diaper in accordance with the present invention is to apply the adhesive to that portion of the backing or facing layer to which the elastic member is to be secured. In assembling the diaper, pressure is applied to the diaper in the region of the elastic member to adhere the facing and backing together between the apertures in the elastic member.

Broadly, the method of manufacturing the elastic structure of the present invention comprises feeding the novel elastic member in a stretched condition between a pair of web surfaces. One of the web surfaces carries an adhesive. The laminate is pressed together and the web surfaces secured to each other through the apertures in the elastic member. The elastic member is then severed and portions allowed to relax.

Referring to FIGS. 11 and 12 of the drawings, there is depicted, in a simplified representation, one method for assembling the components of a disposable diaper in accordance with the present invention. In this embodiment, the backing layer 180, absorbent pad 181 and facing layer 182 are brought together. Just prior to combining the backing and facing layers a pair of elastic members 183 and 184 in accordance with the present invention are inserted along the longitudinal side margins of the backing and facing layers. The elastic members are stretched prior to being combined by running the nip rollers 185 and 186 at a speed slower than that of compressing rollers 187 and 188. Lines of adhesive are applied to the backing layer by nozzles 189. At least one of these lines of adhesive underlie each elastic member. Pressure is applied to the diaper assembly in the region of the elastic members, by passing those regions through the nip of compressing rollers 187 and 188. It is preferred that the surface of one of the rollers be resilient to aid in urging the facing and backing layers into contact with each other between the apertures in the elastic member and assist in securing the facing and backing together through these apertures. The diaper assembly is conveyed to a rotating vacuum cylinder 190 which carries approximately spaced anvils 191 on its surface. The anvils are spaced from each other a distance equal to the desired diaper length. A knife 192 severs individual diapers 193. On severing the diapers, the elastic members are severed in portions wherein the longitudinally extending elastic elements are not transversely connected. The individual diapers are then conveyed away and packaged as is well known.

The foregoing description of the drawings are illustrative and are not to be taken as limiting. Still other variations and modifications are possible without departing from the spirit and scope of the present invention.

I claim:

1. A method for making an elastic structure comprising:
    (a) feeding first and second web substrates to an assembly station;
    (b) feeding an elastic member, comprising a plurality of longitudinally extending elements, intermittent portions of said elements being transversely connected to define apertures therebetween with the portions of the elements between said intermittent portions not being transversely connected, in a stretched condition between said first and second substrates to said assembly station;
    (c) applying adhesive to at least one of said substrates as it is being fed to said assembly station;
    (d) applying pressure to said structure sufficient to adhere said first and second substrates together through the apertures of the intermittent portion of said elastic member, and
    (e) severing said elastic member in a portion wherein the longitudinal elements are not transversely connected and allowing said unconnected elements to relax and return to their unstretched state.

2. A method of intermittently attaching a pair of elastic members intermediate the opposing waistband portions of absorbent pads contained in a continuously moving web of interconnected disposable diapers to form a pair of discrete elastic leg bands in each of said diapers cut from said web, said method comprising the steps of:
    (a) feeding first and second web substrates to an assembly station;
    (b) feeding a pair of stretched elastic members, each member comprising a plurality of longitudinally extending elastic elements, intermittent portions of said elements being interconnected to define apertures therebetween with the portions of said elements between said intermittent portions being non-interconnected, to said assembly station;
    (c) applying adhesive to at least one of said webs as it is being fed to said assembly station, at least a portion of said adhesive being registered such that it will lie within the area occupied by the apertured portions of said stretched elastic members;
    (d) feeding absorbent pad elements having opposing waistband portions with one of said first and second webs;
    (e) adhering said first web and said second web together at said assembly station through the portions of the elastic members defining apertures; and
    (f) cutting said webs transversely into discrete disposable diapers along a line severing said elastic members in non-interconnected portions to allow said non-interconnected portions to relax and return to their unstretched state.

3. A method according to claim 2 wherein adhesive is applied so that a portion of the adhesive also being registered such that it will be within the area occupied by the non-interconnected portions of the stretched elastic members.

* * * * *